United States Patent [19]

Kolozsi

[11] Patent Number: 5,373,854
[45] Date of Patent: Dec. 20, 1994

[54] BIOPSY APPARATUS FOR USE IN ENDOSCOPY

[76] Inventor: William Z. Kolozsi, 1412 Cleveland St., Salem, Ohio 44460

[21] Appl. No.: 92,236

[22] Filed: Jul. 15, 1993

[51] Int. Cl.$^5$ .............................................. A61B 10/00
[52] U.S. Cl. ................................... 128/749; 128/757; 606/208; 606/52; 606/170
[58] Field of Search ............... 128/749, 751, 752, 757; 604/22; 606/205, 206, 207, 208, 209, 51, 52, 170

[56] References Cited

U.S. PATENT DOCUMENTS

| | | | |
|---|---|---|---|
| 2,034,785 | 3/1936 | Wappler | 128/321 |
| 2,868,206 | 1/1959 | Stoesser | 128/303 |
| 3,173,414 | 3/1965 | Guillant | 128/2 |
| 3,840,003 | 10/1974 | Komiya | 128/2 B |
| 3,895,636 | 7/1975 | Schmidt | 128/305 |
| 3,964,468 | 6/1976 | Schulz | 128/2 B |
| 4,038,987 | 8/1977 | Komiya | 128/321 |
| 4,646,751 | 3/1987 | Maslanka | 128/751 |
| 4,662,374 | 5/1987 | Blake, III | 128/325 |
| 4,669,469 | 6/1987 | Gifford et al. | 128/305 |
| 4,669,471 | 6/1987 | Hayashi | 128/321 |
| 4,721,116 | 1/1988 | Schintgen et al. | 128/751 |
| 4,819,635 | 4/1989 | Shapiro | 128/305 |
| 4,881,550 | 11/1989 | Kothe | 128/752 |
| 4,887,612 | 12/1989 | Esser et al. | 128/751 |
| 5,047,041 | 9/1991 | Samuels | 606/159 |
| 5,052,402 | 10/1991 | Bencini et al. | 128/751 |
| 5,069,224 | 12/1991 | Zinnanti, Jr. | 128/752 |
| 5,082,000 | 1/1992 | Picha et al. | 128/750 |
| 5,084,010 | 1/1992 | Plaia et al. | 604/22 |
| 5,133,727 | 7/1992 | Bales et al. | 128/751 |
| 5,135,531 | 8/1992 | Shiber | 606/159 |
| 5,141,519 | 8/1992 | Smith et al. | 606/205 |

*Primary Examiner*—Lee S. Cohen
*Assistant Examiner*—Brian M. Green
*Attorney, Agent, or Firm*—Oldham, Oldham & Wilson

[57] ABSTRACT

An instrument for use in endoscopic biopsy procedures comprising biopsy forceps which utilize a simple and cost effective construction. The apparatus of the invention eliminates the use of an outer housing and utilizes a simplified hinge assembly in conjunction with simple activation of the biopsy jaws. By eliminating the outer housing, the rigid portion of the device is greatly reduced thereby reducing the potential for damage to the instrument or to the narrow channel of the endoscope through which the instrument is inserted and retrieved. The apparatus includes an outer flexible tubular sheath which carries a control wire extending through the sheath. The control wire is movable within the flexible sheath, and includes an operating mechanism coupled to a first end of the tubular sheath for controlling movement of the wire within the sheath. The device further includes a pair of jaw assemblies and a simplified activator for opening and closing the jaws. The control wire actuates the opening and closing of the jaw assemblies and, more specifically, controls an activator for opening and closing the jaw assembly which reduces the number of articulating surfaces or points associated with the jaw assemblies.

17 Claims, 4 Drawing Sheets

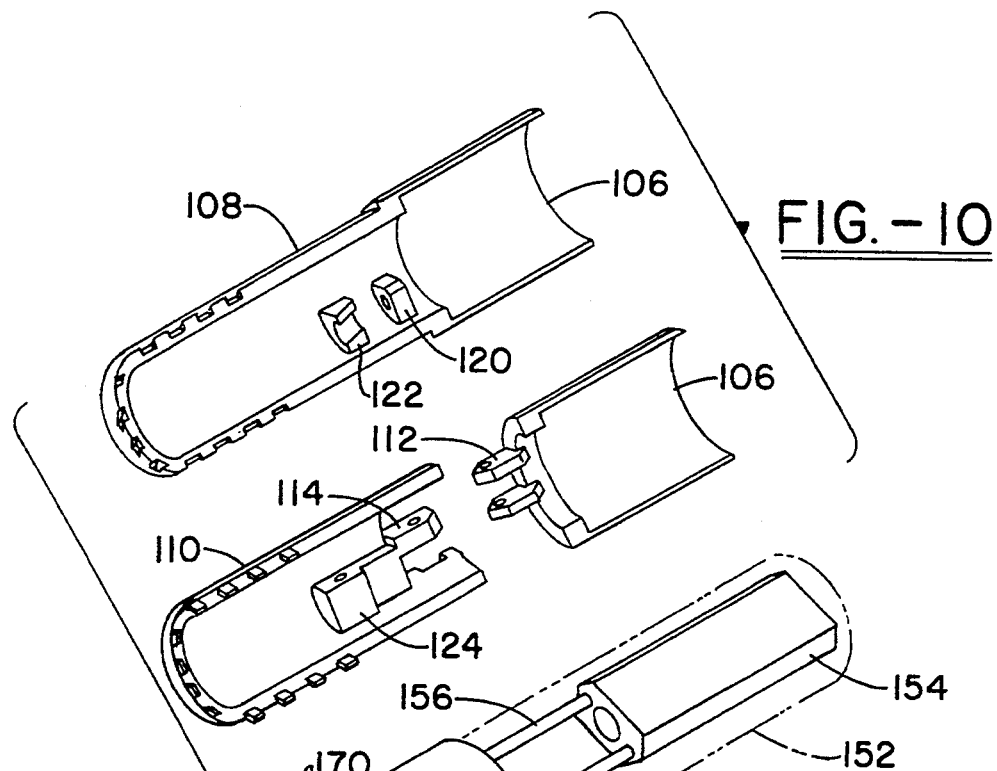
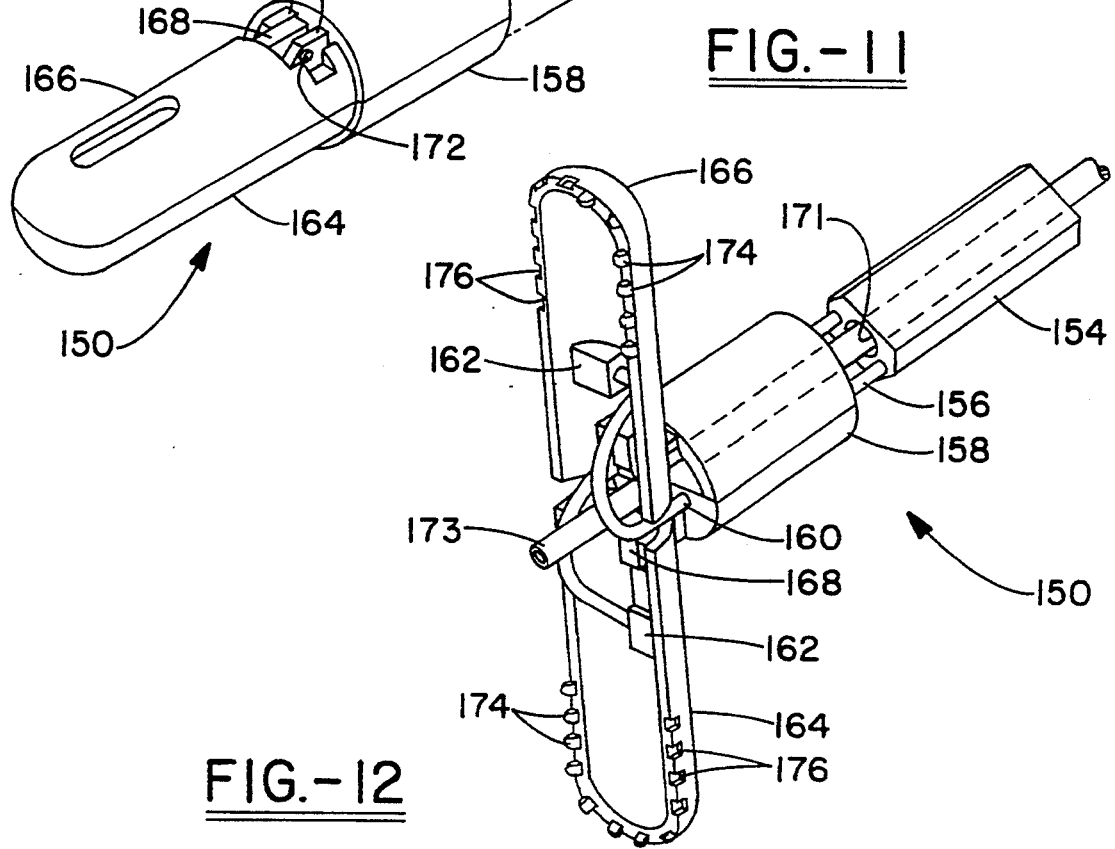

BIOPSY APPARATUS FOR USE IN ENDOSCOPY

TECHNICAL FIELD

The present invention relates to an endoscopic biopsy device for obtaining tissue specimens of the body, and more particularly biopsy forceps and multiple or single biopsy instruments having improved characteristics for biopsy procedures.

BACKGROUND OF THE INVENTION

A variety of endoscopic biopsy forceps have been developed to allow samples of tissue to be taken during endoscopic procedures. Normally, a forceps is inserted together with an endoscope deep into a body cavity being examined, with the forceps adapted to cut and remove body tissue desired for examination. The forceps conventionally used in such procedures have utilized complex arrangements of linkage assemblies and/or camming devices for articulating the jaws of the forceps. As such instruments are of small size, such complexity results in complex machining and manufacturing procedures which greatly increase the cost of such instruments. Thus, present biopsy devices are generally very expensive and, the jaw actuating mechanisms are complex. Additionally, in such prior art devices, a rigid outer housing is normally provided for proper pivoting of the small jaws of the apparatus. Such an outer housing is used to hold the forceps together and must be subsequently removed to allow for a pivot point by means of a pin or screw around which the jaws of the forceps can open or close.

In the prior art, the combination of jaws, linkages, and an outer housing results in an instrument having a significant length thereof which is rigid. This rigidity associated with the instrument increases the potential for damage of the endoscope through which the device is passed to obtain a tissue sample. Endoscopic biopsy procedures require the repeated insertion and removal of the device through a narrow channel in the endoscope in order to obtain a tissue sample. The number of insertions and removals is determined by the number of tissue samples the operator desires to obtain, and each insertion or removal of the device can cause potential damage to the narrow channel of the endoscope or to the biopsy instrument itself.

Further, as many current biopsy devices are intended for multiple use, the possible damage to the endoscope or biopsy device itself is increased with currently-known apparatus. In conventional biopsy forceps, the intended multiple use of the instruments requires extensive cleaning and sterilizing procedures to be performed to comply with medical standards and use of such instruments. In order to be used a multiple number of times, a biopsy instrument must be sterilized by immersing a contaminated instrument in a suitable chemical sterilizing solution, or subjecting the apparatus to sterilization in an autoclave. In either instance, the sterilization and cleaning procedures will often decrease the performance or useful life span of such instruments, due to the complexity of its manufacture. Further, some devices which are intended only for a single use still incorporate complex linkage and/or camming devices for proper movement of the biopsy jaws, which greatly inhibits their use as the costs associated with such instruments are normally still very high.

Other deficiencies of prior art endoscopic biopsy forceps are found in activation of the biopsy jaw for opening and closing of the jaws. Other problems are noted in the jaws will many times crush tissue which may affect examination of the tissue, or require a larger amount of tissue to be removed for examination.

SUMMARY OF THE INVENTION

Based upon the foregoing, there has been found a need to provide an instrument for use in endoscopic biopsy procedures, comprising biopsy forceps which utilize a simple and cost effective construction. The apparatus of the invention eliminates the use of an outer housing and utilizes a simplified hinge assembly in conjunction with a simplified means of activation of the biopsy jaws. By eliminating the outer housing, the rigid portion of the device is greatly reduced thereby reducing the potential for damage to the instrument or to the narrow channel of the endoscope through which the instrument is inserted and retrieved. The apparatus includes an outer flexible tubular sheath which carries a control wire extending through the sheath. The control wire is movable within the flexible sheath, and includes an operating mechanism coupled to a first end of the tubular sheath for controlling the wire within the sheath. The device further includes a pair of jaw assemblies, and simplified means for opening and closing the jaws. The control wire actuates the means to open and close the jaw assemblies, and more specifically controls an activator means for opening and closing of the jaw assembly while reducing the number of articulating surfaces or points associated with the jaw assemblies.

BRIEF DESCRIPTION OF THE DRAWINGS

The objects and advantages of the invention will become apparent upon a further reading of the detailed description in conjunction with the drawings, wherein:

FIG. 10 shows a partial exploded view of the jaw assemblies of the embodiment as shown in FIG. 8;

FIG. 11 shows a perspective view of an alternate embodiment of the invention; and FIG. 12 shows a perspective view of the embodiment of FIG. 11 with the jaw assemblies in an open position.

DETAILED DESCRIPTION OF THE INVENTION

Figure 1:
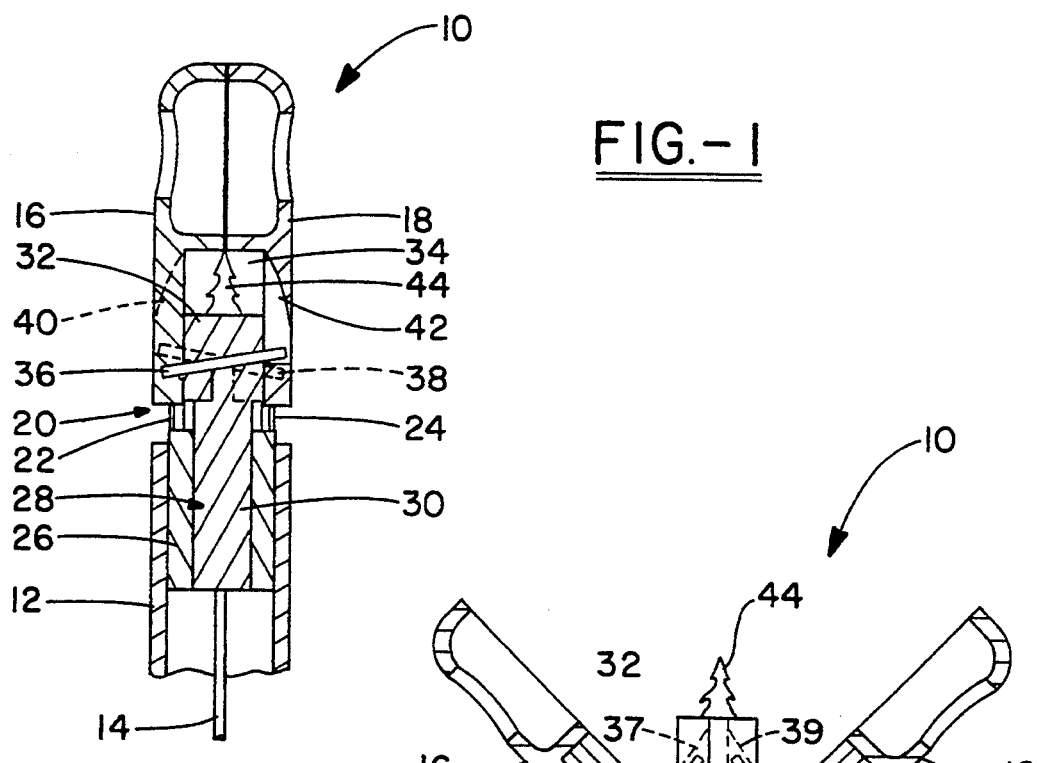
FIG. 1 shows a partial cross-sectional view of a first embodiment of a biopsy apparatus in accordance with the invention.

Turning now to the figures, a first embodiment will be described with reference to FIGS. 1-3, relating to biopsy forceps for use in endoscopy to take tissue specimens of the body. The endoscopic biopsy forceps generally indicated at 10 includes a flexible sheath 12, such as a flexible polymeric tubing, coiled steel or the like, having a first end (not shown) from which control of the forceps device is effected by a doctor or other practitioner. A suitable operating mechanism (not shown) for actuating the forceps device is provided at the first end of the sheath 10 which is connected to a control wire 14. The control wire 14 is longitudinally movable within the sheath 12, and the suitable operating mechanism or means will control movement of the control wire therethrough. The apparatus 10 further includes a pair of biopsy jaw assemblies 16 and 18 disposed adjacent a second end 20 of the sheath 12. The biopsy jaw assemblies 16 and 18 are operatively connected to the control wire 14 by an actuator means, which will be hereinafter more fully described. In the biopsy apparatus, at least one of the jaw assemblies 16 or 18 is movable between open and closed positions with respect to the other of the jaw assemblies, and in this embodiment both jaw assemblies 16 and 18 are movable between open and closed positions as seen in FIGS. 1 and 2.

In each of the embodiments of the invention, the at least one jaw assembly which is movable between open and closed positions has a hinge means associated therewith, which in this embodiment includes a pair of living hinge mechanisms 22 and 24 provided at a position adjacent the exterior surface of the jaw assemblies 16 and 18, and adjacent the second end 20 of the sheath 12. The hinge mechanism of this embodiment allows each of the jaw assemblies 16 and 18 to open relative to one another, and provides a simplified mechanism for proper pivoting of the jaws to an open position for sampling of tissue specimens. The hinges 22 and 24 may be formed in a tubular extension 26 of the forceps 10, which slidably fits into the sheath 12 so as to be frictionally engaged within the second end 20 thereof. Within the tubular extension 26 is also provided a piston 28 which is longitudinally movable within the tubular extension 26 by means of the control wire 14 which is coupled thereto. The piston 28 forms a part of an actuator means, with a body portion 30 thereof forming a connector means which is coupled to the control wire 14. The body portion 30 is longitudinally movable relative to the tubular extension 26 and flexible sheath 12 along with the control wire 14 from a closed position as shown in FIG. 1, to an open position as shown in FIG. 2. The piston assembly 28 also includes a head portion 32 which is longitudinally movable within a cavity 34 formed between the jaw assemblies 16 and 18. The piston head 32 includes a linkage means, which in this embodiment comprise activator pins which are slidably disposed within channels formed within actuator piston head 32. The activator pins 36 and 38 are secured at a first end thereof to a respective one of the jaw assemblies 16 and 18, while the second end of each activator pin 36 and 38 is movable along an arcuate path within slots 40 and 42 formed in each of the jaw assemblies 16 and 18 respectively. As an optional feature, there may also be provided a central spike 44 mounted on top of the actuator piston head 32 to facilitate the taking of tissue samples using the device.

Figure 2:
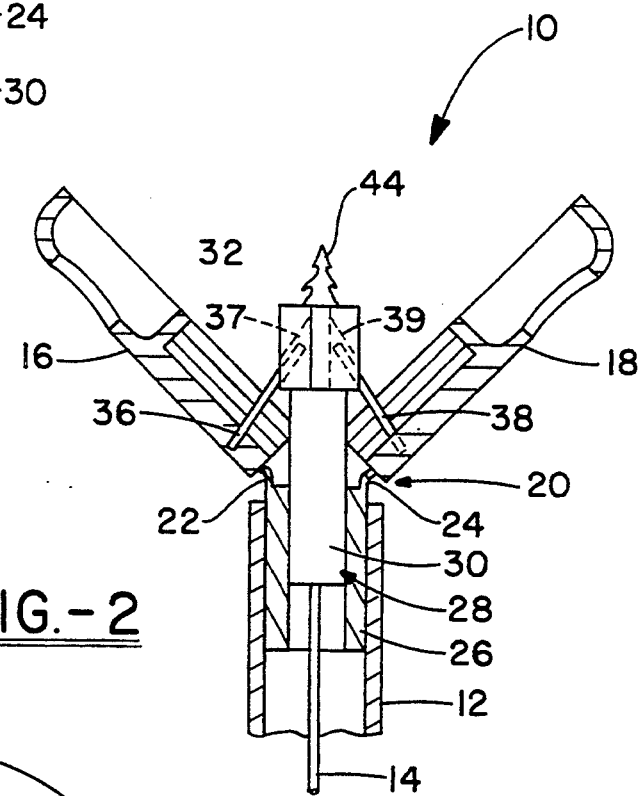
FIG. 2 is a partial cross-sectional view of the embodiment of FIG. 1, showing the jaw assemblies of the apparatus in the open position.
Figure 3:
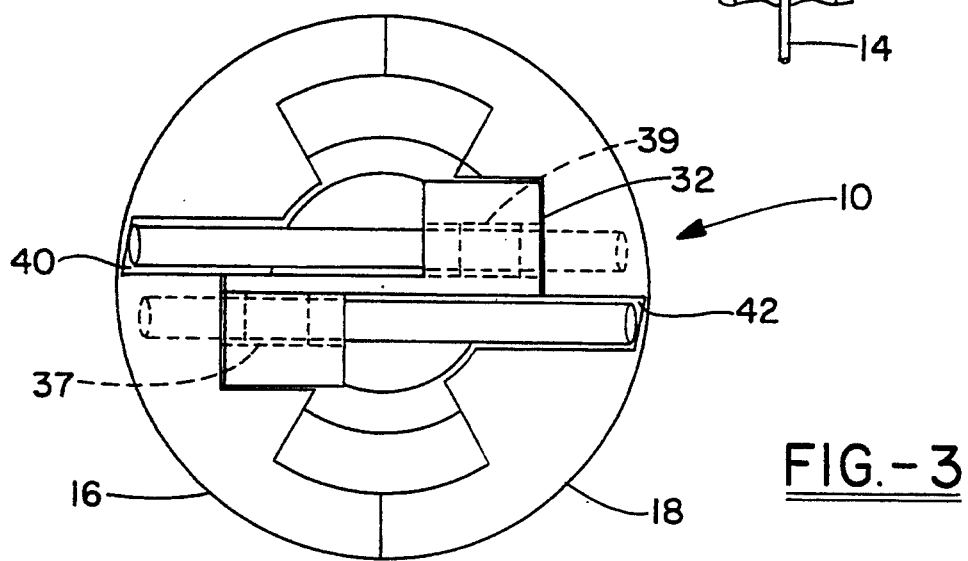
FIG. 3 shows an enlarged top cross-sectional view of the embodiment of FIG. 1.

In operation of the embodiment shown in FIGS. 1-3, articulation of the jaw assemblies 16 and 18 from a closed position shown in FIG. 1 to the open position shown in FIG. 2 is performed by the actuator means including the actuator piston assembly 28 and associated linkage means comprising activator pins 36 and 38. It should be recognized that upon outward longitudinal movement of the piston body 30 upon force being applied through control wire 14 will result in piston head 32 traveling upwardly within cavity 34. Upon upward movement of the piston head 32, the second end of actuator pins 36 and 38 will be forced upwardly along the arcuate path within slots 40 and 42 respectively. The activator pins 36 and 38 will also slide within channels 37 and 39 in a manner such that the first ends of each of the activator pins 36 and 38 which are fixed to one of the jaw assemblies 16 and 18 will be forced outwardly to apply an outward biasing force on the jaw assemblies 16 and 18. In this manner, articulation of jaws 16 and 18 to their open position about the hinge mechanisms 20 and 22 provide a simplified apparatus which does not require complex arrangements of linkage assemblies and/or camming devices for articulation of the jaws of the forceps. Closing of the jaw assemblies is effected by longitudinal movement of the piston 28 from the position as shown in FIG. 2 to the position as shown in FIG. 1 by merely retracting the control wire 14. It should also be recognized that the jaw assemblies 16 and 18 can be maintained in the closed position by retraction of the control wire 14, thereby eliminating an outer rigid housing which has been used in the prior art. By reducing the rigid portion of the device, the potential for damage to the narrow channel of an endoscope through which the biopsy device is inserted is greatly minimized. The construction is also very cost effectively manufactured, such that the biopsy device 10 is suitable for single patient use, which would eliminate requirements for cleaning and sterilization of the device between patient uses. The mechanism for opening and closing of the jaw assemblies has been greatly simplified compared to known systems which require a complexity of articulating points held together by pins or screws. The living hinge mechanism which can be utilized in association with this embodiment is easily and cost effectively manufactured by molding or simplified machining to achieve these advantages. The biopsy jaw assemblies 16 and 18 may themselves be molded from a polymeric or other suitable material.

Figure 4:
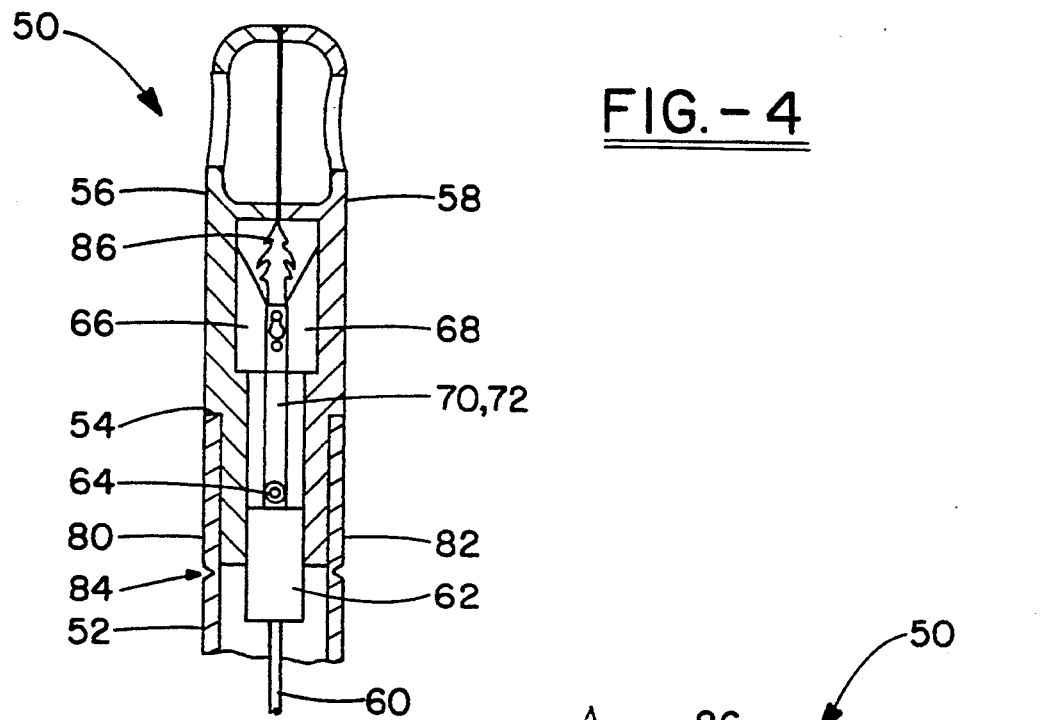
FIG. 4 shows a partial cross-sectional view of an alternate embodiment of the invention.
Figure 5:
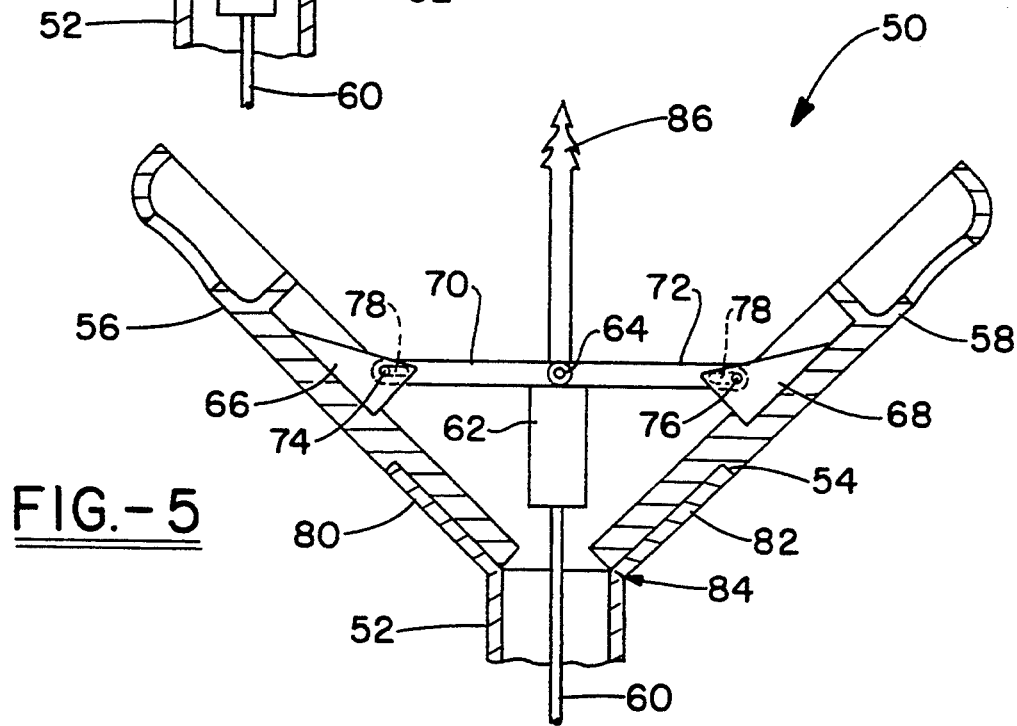
FIG. 5 shows a partial cross-sectional view of the embodiment of FIG. 4, with the jaw assemblies in the open position.
Figure 6:
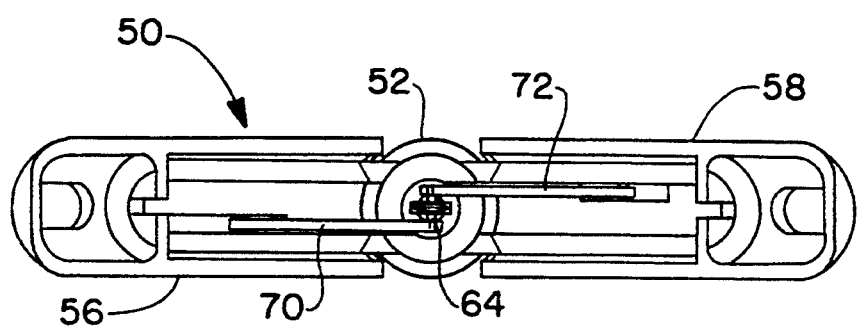
FIG. 6 shows a top elevational view of the embodiment as shown in FIG. 5.

In an alternative embodiment of the invention as shown in FIGS. 4-6, the use of an outer housing to hold the jaw assemblies of the biopsy apparatus in a closed position is again eliminated. In this embodiment, the biopsy apparatus generally designated 50, again includes a flexible sheath 52 having a remote first end and a second end 54 into which a pair of jaw assemblies 56 and 58 are engaged. The sheath 52 may be either a flexible plastic or coiled steel, and carries a longitudinally movable control wire 60 therein. The control wire 60 is attached by a connector 62 which in turn is pivotally attached to each of the jaw assemblies 56 and 58 about a connector pin 64. More specifically, each of the jaw assemblies 56 and 58 include actuator arms 66 and 68 respectively, which are coupled to the connector through a pair of linkage rods or arms 70 and 72, which themselves are pivotally engaged to connector pin 64. Each of the linkage arms 70 and 72 are coupled to the actuator arms 66 and 68 by means of pivot pins 74 and 76. The linkage arms 70 and 72 each include a slot 78 which allows relative movement between the arms 70 and 72 and the pivot pins 74 and 76 and respective actuator arms 66 and 68.

In this embodiment, actuation of the apparatus 50 to obtain a tissue sample is effected by means of the control wire 60. The articulation points for each of the jaw assemblies 56 and 58 may be formed integrally with the outer sheath 52 in which the jaw assemblies are positioned. As seen in FIGS. 4 and 5, a pair of hinge flaps 80 and 82 are formed by hinge points 84 provided in the sheath 52. The hinge points 84 may be integrally formed during manufacture of the sheath 52 such as by molding or the like, or may be provided by cutting of the sheath 52 an amount to allow hinge flaps 80 and 82 to articulate about the point 84. Each of the jaw assemblies 56 and 58 are secured to the respective hinge flap 80 or 82 to allow articulation thereof about point 84. As seen in FIG. 5, upon longitudinal movement of the control wire toward end 54 of the sheath 52, the linkage arms 70 and 72 will force each of the jaw assemblies 56 and 58 outwardly while rotating about the respective connector pins 64, 74, and 76. A central spike 86 may be optionally provided to facilitate the taking of tissue samples in association with the jaw assemblies 56 and 58.

Figure 7:
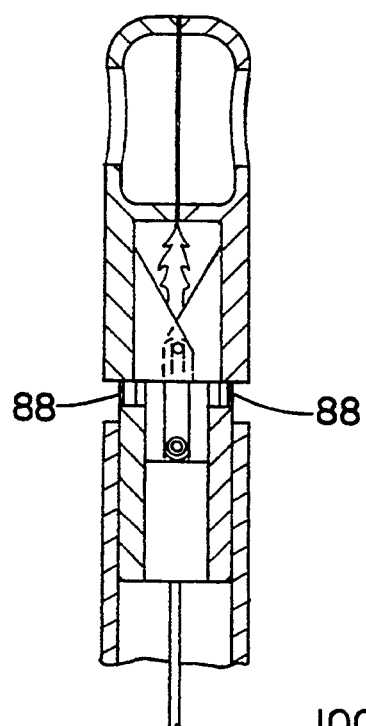
FIG. 7 shows a partial cross-sectional view of another alternate embodiment of the invention.

The structure of this embodiment utilizes a hinge outside catheter or a separate piece which is attached to the hollow tubular sheath of the biopsy apparatus. The opening and closing of the jaw assemblies associated with the apparatus are effected by a hinge flap mechanism to which each of the jaw assemblies are secured, so as to eliminate any requirement for an outer housing to articulate the jaw assemblies. The design greatly reduces the number of parts required for manufacture, and reduces the complexity of the assembly. Although the hinge mechanism of the embodiment is shown to be formed in the outer tubular sheath, a living hinge may also be incorporated as part of a molded jaw assembly as shown in FIG. 7. In FIG. 7, the hinge points for each of the jaw assemblies are integrally formed in association with the jaw assemblies at 88. The hinge points 88 may be a living hinge formed integrally with each the jaw assemblies 56 and 58 or otherwise as desired. In other respects, the embodiment of FIG. 7 operates substantially as that shown in FIGS. 4–6. In each of these embodiments, the biopsy apparatus eliminates an outer housing required to articulate the cups and therefore reduces any rigid portion which will in return reduce damage to the narrow channel of the endoscope with which the apparatus is utilized.

Figure 8:
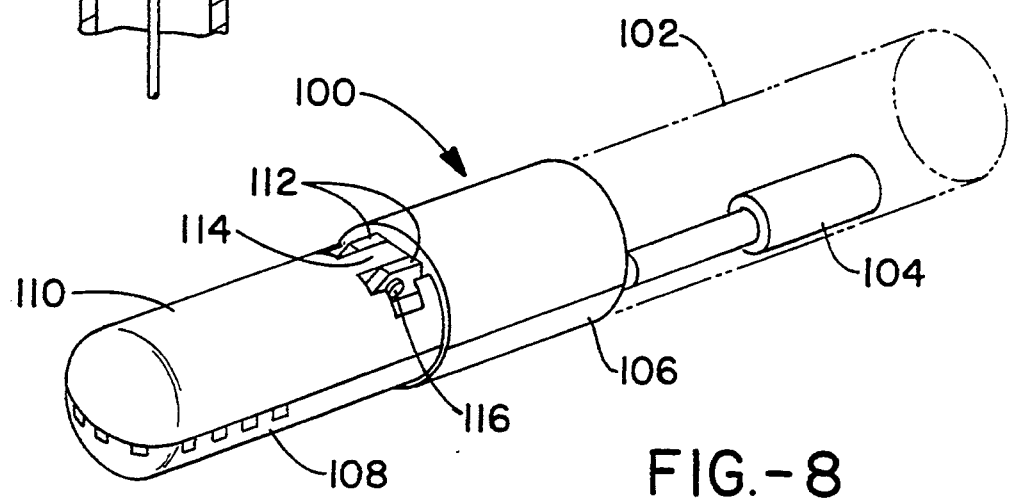
FIG. 8 shows a partial perspective view of yet another alternate embodiment of the invention.
Figure 9:
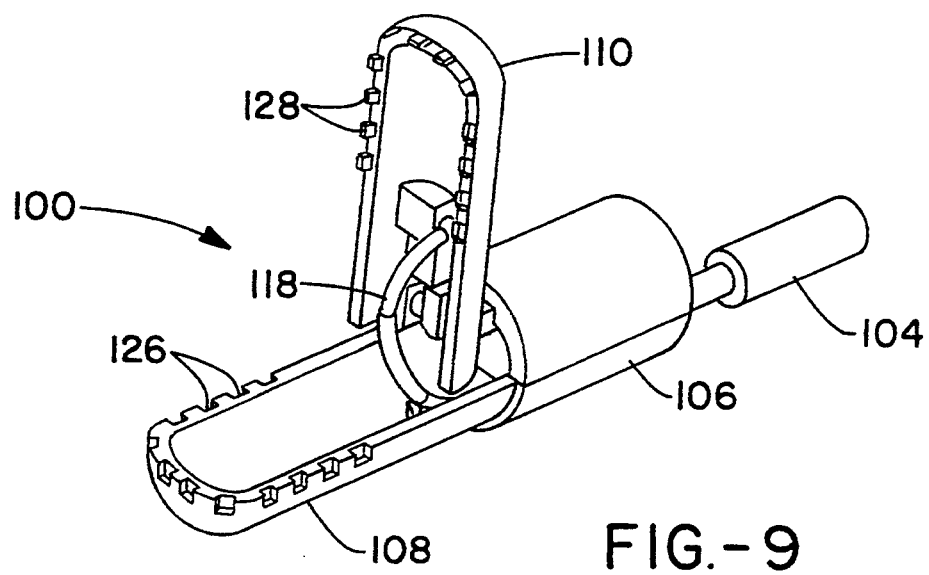
FIG. 9 shows a perspective view of the embodiment of FIG. 8, with the jaw assembly in an open position.

Turning now to FIGS. 8–10, another embodiment of the invention will be described. In this embodiment, a multiple biopsy apparatus 100 is shown, adapted to be used a multiplicity of times in association with an endoscope. In this embodiment, the apparatus 100 again includes a tubular sheath 102 (shown in phantom) to which a biopsy head is attached. The biopsy apparatus is secured within sheath 102, which also carries a longitudinally movable control wire (not shown) which is coupled to a wire coupler 104. The apparatus 100 includes a hinge collar 106 disposed at the end of sheath 102, which in turn is connected to or integral with a fixed jaw assembly 108. The hinge collar 106 also pivotably connects a movable jaw assembly 110, which is used in conjunction with fixed jaw assembly 108 to obtain samples of body tissue. In this embodiment, the hinge collar 106 includes hinge supports 112 which pivotally engage a hinge arm 114 associated with movable jaw assembly 110. A hinge pin 116 or other suitable means may be used to pivotably couple movable jaw 110 with hinge collar 106. Further in this embodiment, the wire coupler 104 includes a connecting wire 118, which is also longitudinally movable within hinge collar 106. The connecting wire 118 and associated wire coupler 104 are to be coupled to the activation wire (not shown) extending through tubular sheath 102 for operation of the biopsy apparatus. With reference to FIG. 10, the connecting wire 118 is fed through a closed wire guide 120 associated with the fixed jaw assembly 108, and is also guided by an open wire guide 122 positioned adjacent the closed wire guide 120. The connecting wire 118 is thereafter coupled to movable jaw assembly 110 by means of an outwardly extending coupling member 124 associated therewith. In operation, as seen in FIG. 9, longitudinal movement of an activation wire extending through sheath 102 will impart longitudinal movement to wire coupler 104 and the connecting wire 118 accordingly. Connecting wire 118 is guided by guide members 120 and 122 so as to apply an outward force onto the movable jaw assembly 110 at coupling site 124. The wedge shape of guide member 122 forces connecting wire 118 toward movable jaw assembly 110 to perform opening of the biopsy apparatus for obtaining tissue samples. Again, the arrangement provides for opening and subsequent closing of the movable jaw assembly 110 relative to the fixed jaw assembly 108 in a simplified and cost effective manner.

In this embodiment, the hinge assembly of the apparatus is positioned on the side of the device rather than other conventional pivot points, and utilizes wire guides to impart desired opening and closing forces to the movable jaw assembly. The apparatus utilizes one fixed and one movable jaw assembly, to simplify its construction while still providing simplified tissue sampling. Also in this embodiment, the hinge collar 106 and associated fixed jaw assembly 108 form a space therebetween to allow for the application of suction through sheath 102 to pull tissue to be sampled into the apparatus when movable jaw assembly 110 is in the open position. Also in this embodiment, the fixed jaw assembly 108 is shown to include a plurality of notches or indentations 126 which matingly engage a plurality of teeth 128 formed on the movable jaw assembly 110. This arrangement of teeth and indentations provides a mechanism for shearing of tissue from a body rather than crushing the tissue as is normally performed with conventional forceps. It should also be understood that the slots 126 may be provided on the movable jaw assembly while teeth 128 are formed on the fixed jaw assembly, or each being disposed on both jaw assemblies if desired.

Another alternative embodiment of the invention is shown in FIGS. 11 and 12, wherein a single biopsy apparatus 150 is shown to include a tubular sheath 152 (shown in phantom), similar to the other embodiments of the invention. This embodiment is similar to that shown in FIGS. 8–10, but includes two movable jaw assemblies. Again, in this embodiment, a wire coupler 154 will be secured to an activation wire (not shown) extending through sheath 152 and longitudinally movable with respect thereto. The wire coupler 154 in turn includes a pair of activation wires 156 which extend through and are longitudinally movable with respect to a hinge collar 158. The activation wires 156 are guided through apertures 160 formed in hinge collar 158, and are thereafter coupled to coupling members 162 provided internally of each of the movable jaw assemblies 164 and 166. The movable jaw assemblies 164 and 166 each include a hinge arm 168 which is pivotably coupled to hinge members 170 extending from hinge collar 158. A hinge pin 172 may be used to pivotably couple the hinge arms 168 accordingly. It should be recognized that longitudinal movement of a control wire through sheath 152 will in turn cause longitudinal movement of the wire coupler 154 and activation wires 156. The longitudinal movement of activation wires 156 along with their guided travel in the apparatus will cause opening of the movable jaw assemblies 164 and 166 to obtain tissue samples. As shown in FIG. 12, opening or hole 171 may be provided through the wire coupler 154 to allow tube 173 to be inserted into a space between the jaw assemblies 164 and 166. Vaccuum may be applied through tube 173 to facilitate the taking of tissue samples. Again in this embodiment, a series of teeth 174 and associated slots or indentations 176 may be provided on each of the movable jaw assemblies 164 or 166, or alternatively on opposed jaw assemblies similar to the embodiment of FIG. 8 as desired. The teeth 174 in association with indentations 176 provide shearing of tissue rather crushing as previously described. The apparatus 150 as described in this embodiment may be used as a single biopsy apparatus, in that it is simple and cost effectively manufactured to allow disposal thereof after use with a single patient.

Although the invention has been described with reference to particular preferred embodiments thereof, it should be recognized that various modifications or alternative constructions would occur to those skilled in the art, and such modifications or alternatives are contemplated within the scope of the invention. Accordingly, the invention is not to be limited to the above-described embodiments, but is only limited by the appended claims.

What is claimed is:

1. A biopsy apparatus for obtaining tissue samples from a body, comprising:

a flexible sheath having a longitudinal axis and first and second ends and including a control wire extending therethrough, said control wire being longitudinally movable within said sheath;

means at said first end of said sheath to control longitudinal movement of said control wire therethrough;

a pair of biopsy jaw assemblies positioned adjacent said second end of said sheath;

at least one of said jaw assemblies being movable between open and closed positions with respect to the other of said jaw assemblies, said at least one jaw assembly having a hinge means as a part of an outside wall of said at least one jaw assembly to allow pivotal movement of said at least one jaw assembly about a pivot point on said outside wall of said at least one jaw assembly;

actuator means for coupling said pair of biopsy jaw assemblies to said control wire, said actuator means including coupling means to couple said actuator means to said control wire, said coupling means being longitudinally movable relative to said sheath along with said control wire, and linkage means secured to said at least one movable jaw assembly and coupled with said coupling means for acting on said at least on jaw assembly to apply force outwardly or inwardly relative to said at least one jaw assembly during longitudinal movement of said control wire to open and close said at least one jaw assembly.

2. The biopsy apparatus of claim 1, wherein, said pair of biopsy jaw assemblies include a tubular extension which is secured within said sheath at said second end thereof, and said hinge means associated with said at least one jaw assembly is formed in said tubular extension adjacent said second end and the exterior of said tubular extension to allow pivotal movement of said at least one jaw assembly relative to said tubular extension.

3. The biopsy apparatus of claim 2, wherein, said hinge means comprises an integrally formed hinge within said tubular extension.

4. The biopsy apparatus of claim 1, wherein, said actuator means comprises a piston disposed within said pair of biopsy jaw assemblies, wherein said coupling means comprises a body portion of said piston which is coupled to said control wire, said piston being longitudinally movable within said pair of biopsy jaw assemblies, wherein said linkage means is provided in a head portion of said piston to apply force outwardly or inwardly on said at least one jaw assembly upon longitudinal movement of said piston within said pair of biopsy jaw assemblies.

5. The biopsy apparatus of claim 4, wherein, said linkage means includes at least one activator pin having first and second ends, with a first end thereof secured to said at least one movable jaw assembly, and a second end thereof disposed within a channel formed in said piston head, such that upon longitudinal movement of said piston head, said at least one activator pin will be caused to move within said channel so as to urge said first end outwardly or inwardly depending upon relative longitudinal movement of said piston head.

6. The biopsy apparatus of claim 1, wherein, said hinge means associated with said at least one movable jaw assembly comprises a portion of said sheath which is pivotable relative to said longitudinal axis of said sheath, with said at least one movable jaw assembly being secured to said portion of said sheath so as to be pivotable in conjunction therewith.

7. The biopsy apparatus of claim 6, wherein, said hinge means is formed as an integral hinge in said sheath.

8. The biopsy apparatus of claim 1, wherein, said actuator means includes at least one linkage arm having first and second ends, the first end thereof being coupled to said coupling means and the second end thereof being coupled to an actuator arm associated with said at least one jaw assembly, said linkage arm being pivotably coupled to both said connector means and said actuator arm such that upon longitudinal movement of said coupling means, said at least one linkage arm will rotate about said first end to apply said force to said at least one jaw assembly through said actuator arm thereof.

9. The biopsy apparatus of claim 8, wherein, said at least one linkage arm includes a slot at said second end thereof which allows predetermined relative movement between said linkage arm and said actuator arm to which it is coupled.

10. The biopsy apparatus of claim 1, wherein, both of said pair of biopsy jaw assemblies are movable between open and closed positions with respect to the other of said jaw assemblies, with said actuator means acting on each of said jaw assemblies to apply force outwardly or inwardly to effect opening or closing of each of said jaw assemblies.

11. The biopsy apparatus of claim 1, further comprising,
spike means disposed between said pair of biopsy jaw assemblies, which will be exposed upon opening of said at least one jaw assembly to facilitate the taking of tissue samples in association with said jaw assemblies.

12. The biopsy apparatus of claim 1, wherein,
said hinge means comprises a hinge collar associated with said pair of jaw assemblies which includes hinge support means, with said at least one movable jaw assembly having a hinge arm which is pivotably coupled to said hinge support means of said hinge collar to allow pivotable movement of said at least one moveable jaw assembly relative to said hinge collar.

13. The biopsy apparatus of claim 1, wherein,
said pair of biopsy jaw assemblies include a plurality of teeth and corresponding slots in an opposed one of said jaw assemblies, which will provide shearing of tissue upon closing of said jaw assemblies.

14. The biopsy apparatus of claim 1, wherein,
a channel is provided through said coupling means to said pair of biopsy jaw assemblies to allow insertion of means to apply suction in a region adjacent said at least one movable jaw assembly to facilitate taking of tissue samples.

15. A biopsy apparatus for obtaining tissue samples from a body, comprising:
a flexible sheath having a longitudinal axis and first and second ends and including a control wire extending therethrough, said control wire being longitudinally movable within said sheath;
means at said first end of said sheath to control longitudinal movement of said control wire therethrough;
a pair of biopsy jaw assemblies positioned adjacent said second end of said sheath;
at least one of said jaw assemblies being movable between open and closed positions with respect to the other of said jaw assemblies, said at least one jaw assembly having a hinge means as a part of an outside wall of said at least one jaw assembly to allow pivotal movement of said at least one jaw assembly about a pivot point on said outside wall of said at least one jaw assembly;
actuator means for coupling said pair of biopsy jaw assemblies to said control wire, said actuator means including coupling means to couple said actuator means to said control wire, said coupling means being longitudinally movable relative to said sheath along with said control wire, and linkage means secured to said at least one movable jaw assembly and coupled with said coupling means for acting on said at least on jaw assembly to apply force outwardly or inwardly relative to said at least one jaw assembly during longitudinal movement of said control wire to open and close said at least one jaw assembly, wherein said actuator means further includes at least one connecting wire secured to said coupling means and extending through at least one guide means which directs said at least one connecting wire outwardly toward said at least one movable jaw assembly, such that upon longitudinal movement of said coupling means, said at least one connecting wire will apply said force outwardly or inwardly relative to said at least one movable jaw assembly.

16. The biopsy apparatus of claim 15, wherein,
said at least one connecting wire is fed through a first closed wire guide and thereafter through an open wire guide, wherein said open wire guide has a wedge shape which forces said connecting wire outwardly relative thereto.

17. The biopsy apparatus of claim 15, wherein,
said guide means comprises at least one aperture formed in a hinge collar associated with said pair of jaw assemblies through which said at least one connecting wire passes.

* * * * *